(12) United States Patent
Chen et al.

(10) Patent No.: US 7,763,308 B2
(45) Date of Patent: Jul. 27, 2010

(54) METHOD OF REGULATING TEMPERATURE OF A COMPOSITION FOR COATING IMPLANTABLE MEDICAL DEVICES

(75) Inventors: Yung-Ming Chen, Cupertino, CA (US); Charles R. Bobson, San Mateo, CA (US); John F. LoPrete, San Carlos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1441 days.

(21) Appl. No.: 11/011,365

(22) Filed: Dec. 13, 2004

(65) Prior Publication Data

US 2005/0098097 A1 May 12, 2005

Related U.S. Application Data

(62) Division of application No. 09/966,590, filed on Sep. 27, 2001, now abandoned.

(51) Int. Cl.
*B05D 3/02* (2006.01)
*B05B 7/16* (2006.01)

(52) U.S. Cl. .............. 427/2.1; 427/2.24; 427/2.25; 118/666; 118/667; 118/302; 222/146.2; 222/146.5

(58) Field of Classification Search .............. 427/2.1, 427/2.24, 2.25; 118/666, 667, 302; 222/146.2, 222/146.5
See application file for complete search history.

(56) References Cited

U.S. PATENT DOCUMENTS

| | | | |
|---|---|---|---|
| 2,647,017 A | 7/1953 | Coulliette | |
| 4,132,357 A * | 1/1979 | Blackinton | 239/11 |
| 4,733,665 A | 3/1988 | Palmaz | |
| 4,800,882 A | 1/1989 | Gianturco | |
| 4,886,062 A | 12/1989 | Wiktor | |
| 4,932,353 A | 6/1990 | Kawata et al. | |
| 4,967,606 A | 11/1990 | Wells et al. | |
| 5,015,505 A | 5/1991 | Cetnar | |
| 5,127,362 A | 7/1992 | Iwatsu et al. | |
| 5,225,750 A | 7/1993 | Higuchi et al. | |
| 5,368,560 A | 11/1994 | Rambo et al. | |
| 5,464,650 A | 11/1995 | Berg et al. | |
| 5,511,726 A | 4/1996 | Greenspan et al. | |

(Continued)

FOREIGN PATENT DOCUMENTS

EP 0 970 711 1/2000

(Continued)

OTHER PUBLICATIONS

"Impulse Jetting: About Us," http://www.impulsejetting.com/about.html, printed Dec. 18, 2000 (1 page).

(Continued)

*Primary Examiner*—Timothy H Meeks
*Assistant Examiner*—Cachet I Sellman
(74) *Attorney, Agent, or Firm*—Squire, Sanders & Dempsey, L.L.P.

(57) ABSTRACT

An applicator for applying a coating substance to an implantable medical device, such as a stent, is provided. The applicator comprises a nozzle and a temperature controller in communication with the nozzle for adjusting the temperature of the coating substance. A method of using the applicator is also provided.

31 Claims, 1 Drawing Sheet

U.S. PATENT DOCUMENTS

| | | | |
|---|---|---|---|
| 5,527,337 | A | 6/1996 | Stack et al. |
| 5,700,286 | A | 12/1997 | Tartaglia et al. |
| 5,711,989 | A * | 1/1998 | Ciardella et al. ............... 427/8 |
| 5,713,949 | A | 2/1998 | Jayaraman |
| 5,741,554 | A | 4/1998 | Tisone |
| 5,766,710 | A | 6/1998 | Turnlund et al. |
| 5,769,883 | A | 6/1998 | Buscemi et al. |
| 5,824,056 | A | 10/1998 | Rosenberg |
| 5,837,313 | A | 11/1998 | Ding et al. |
| 5,843,172 | A | 12/1998 | Yan |
| 5,869,127 | A | 2/1999 | Zhong |
| 5,873,904 | A | 2/1999 | Ragheb et al. |
| 5,980,972 | A * | 11/1999 | Ding .................. 427/2.24 |
| 5,984,449 | A | 11/1999 | Tajika et al. |
| 6,056,993 | A * | 5/2000 | Leidner et al. ........... 427/2.25 |
| 6,067,480 | A * | 5/2000 | Stuffle et al. ............. 700/109 |
| 6,096,070 | A | 8/2000 | Ragheb et al. |
| 6,121,027 | A | 9/2000 | Clapper et al. |
| 6,132,809 | A | 10/2000 | Hynes et al. |
| 6,159,142 | A * | 12/2000 | Alt ............................ 600/3 |
| 6,209,621 | B1 | 4/2001 | Treacy |
| 6,214,407 | B1 | 4/2001 | Laube et al. |
| 6,224,675 | B1 | 5/2001 | Prentice et al. |
| 4,733,665 | C2 | 1/2002 | Palmaz |
| 6,395,326 | B1 * | 5/2002 | Castro et al. ............. 427/2.24 |
| 6,419,745 | B1 * | 7/2002 | Burkett et al. ............. 118/125 |
| 6,462,284 | B1 | 10/2002 | Hashimoto |
| 6,491,666 | B1 | 12/2002 | Santini, Jr. et al. |
| 6,743,462 | B1 * | 6/2004 | Pacetti ..................... 427/2.24 |
| 2002/0122877 | A1 * | 9/2002 | Harish et al. ............. 427/2.24 |
| 2002/0182316 | A1 * | 12/2002 | Gilliard et al. ............. 427/162 |

FOREIGN PATENT DOCUMENTS

| | | |
|---|---|---|
| WO | WO 98/23228 | 6/1998 |
| WO | WO 01/45763 | 6/2001 |
| WO | WO 01/52772 | 7/2001 |

OTHER PUBLICATIONS

"Impulse Jetting: Our Technology," http://www.impulsejetting.com/tech1.html, printed Dec. 18, 2000 (1 page).

Kirk Othmer, "Coating Processes-Spray Coating", Encyclopedia of Chemical Technology, $3^{rd}$ Ed. vol. 6, pp. 414-418.

Trident, Inc., http://www.tridetintl.com/subbody.html, printed Dec. 18, 2000 (4 pages).

World Precision Instruments, Inc., "Nanoliter 2000," http://www.wpi-europe.com/pumps/Nanoliter_Injector.html, printed Sep. 30, 2002 (4 pages).

World Precision Instruments, Inc., "Nonolite Injector," http://www.wpiinc.com/WPI_Web/Pumps/Nanoliter_Injector.html, printed Sep. 30, 2002 (3 pages).

World Precision Instruments; Inc:, "Pneumatic PicoPumps," httm://www.wpi-europe.com/pumps/Pneumatic_PicoPumps.html, printed Sep. 30, 2002 (7 pages).

World Precision Instruments, Inc., "Pneumatic PicoPumps," http://www.wpiinc.com/WPI_Web/Pumps/Pneumatic_PicoPumps.html, printed Sep. 30, 2002 (6 pages).

World Precision Instruments, Inc., http://www.wpiinc.com/WPI_Web/Pumps/pneumatic_Fig.gif, printed Sep. 30, 2002 (1 page).

* cited by examiner

METHOD OF REGULATING TEMPERATURE OF A COMPOSITION FOR COATING IMPLANTABLE MEDICAL DEVICES

CROSS REFERENCE

This is a divisional application of U.S. Ser. No. 09/966,590, which was filed on Sep. 27, 2001, now abandoned and claims the priority benefit of that application. This divisional application hereby incorporates by reference the complete contents of U.S. Ser. No. 09/966,590.

BACKGROUND OF THE INVENTION

1. Field of the Invention

This invention relates to an apparatus for applying a composition to an implantable device such as a stent and method for using the same to form a coating.

2. Description of the Background

Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location. Mechanical intervention via stents has reduced the rate of restenosis; restenosis, however, is still a significant clinical problem. Accordingly, stents have been modified to perform not only as a mechanical scaffolding, but also to provide biological therapy.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

A common method of medicating a stent is by depositing a polymeric coating, impregnated with the therapeutic substance, on the surface of the stent. A polymer dissolved in a solvent is applied to the stent. A therapeutic substance can be dissolved or dispersed in the composition. The solvent is allowed to evaporate to form the coating. The application of the composition can be performed by spraying the composition on the stent or immersing the stent in the composition.

Problems associated with coating stents with a polymeric coating include formation of polymer "cob webs" between the stent struts, excessive gathering of clumps or "pool webs" of coating on the surface of the stent struts, and lack of uniformity of the coating. What is needed is, accordingly, an apparatus and process for coating stents that minimizes or significantly reduces the aforementioned defects.

SUMMARY OF THE INVENTION

In accordance with one aspect of the invention, an applicator for applying a coating substance to an implantable medical device, such as a stent, is provided. The applicator comprises a nozzle and a temperature controller in thermal communication with the nozzle for adjusting the temperature of the coating substance during the application process. In one embodiment, the temperature controller circumscribes the nozzle and is position in close proximity to an orifice of the nozzle through which the coating substance is applied. The coating substance can be a polymer dissolved in a solvent and optionally a therapeutic substance added thereto.

In accordance with another aspect of the invention, an apparatus for applying a composition to a stent is provided comprising an applicator for spraying a composition at the stent, and a temperature controller connected to the applicator for adjusting the temperature of the composition to a temperature other than room temperature. The applicator can include a body extending into a nozzle, such that the temperature controller is positioned in close proximity to the nozzle. The applicator can be an air-assisted internal or external mixing atomizer. The apparatus can additionally include a temperature modulator in communication with the temperature controller for maintaining the temperature of the composition at a constant level during the application of the composition.

In accordance with another aspect of the invention, a method of coating a stent is provided comprising positioning a stent at a distance away form a nozzle, applying a coating substance from the nozzle to the stent, and adjusting the temperature of the nozzle to adjust the temperature of the composition. The temperature of the nozzle can be adjusted to a temperature above room temperature, e.g., 35° C. to about 40° C.

DETAILED DESCRIPTION OF THE EMBODIMENTS

Dispenser Assembly

Figure 1:
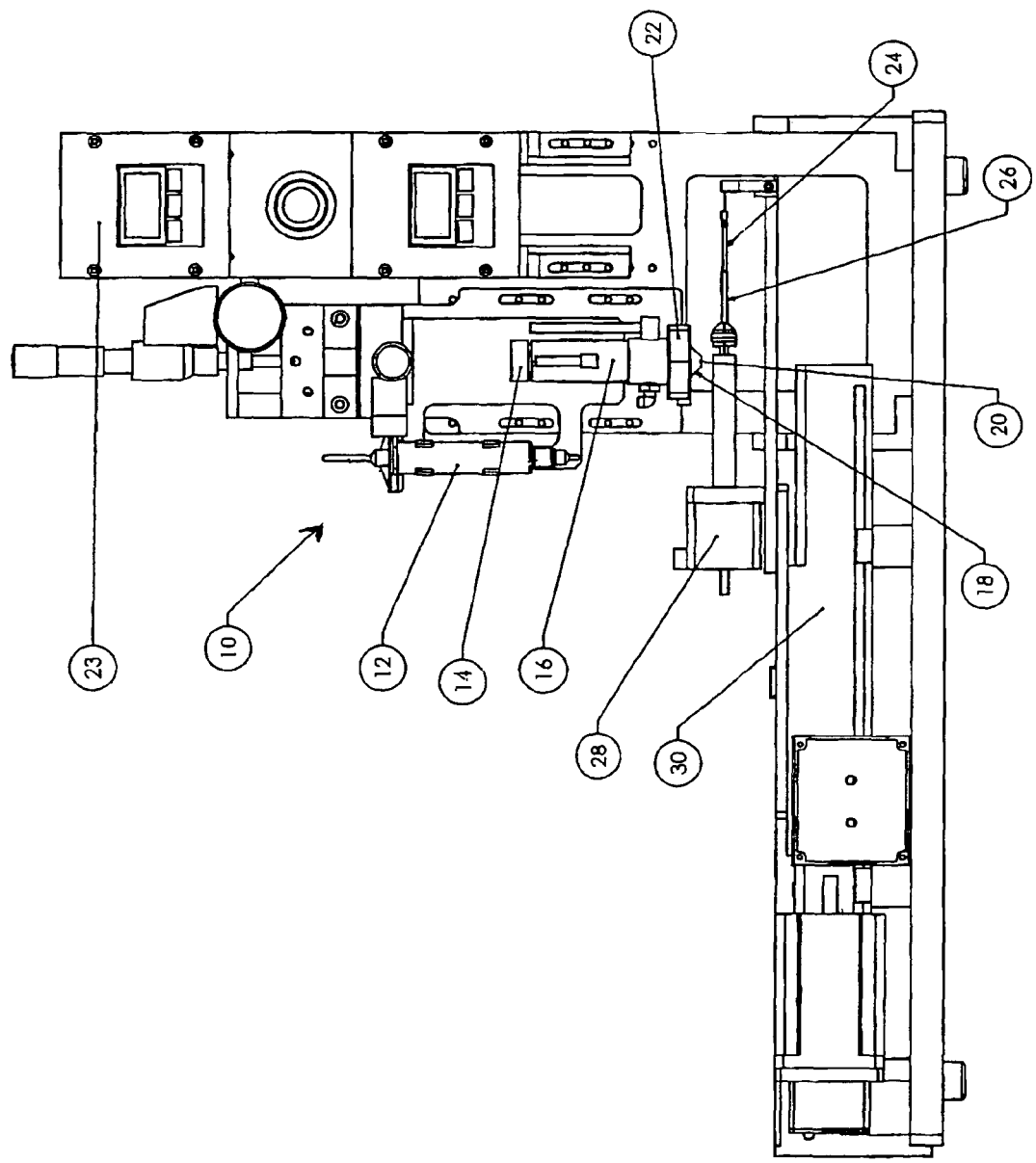
FIG. 1 illustrates an apparatus used to coat a stent in accordance with one embodiment of the invention.

Referring to FIG. 1, there is illustrated a dispenser assembly 10 for applying a composition to a medical device. Dispenser assembly 10 includes a source or solution barrel 12 for containing and supplying a coating composition to an applicator 14. Applicator 14 can include a body 16 and a nozzle 18 extending from body 16. Nozzle 18 includes an orifice 20 of any suitable size for allowing a composition to be sprayed from the applicator 14. Applicators are commercially available from Spray Systems Co., EFD International Inc., and Badger Air-Brush Co., one specific model of which is the EFD 780S spray device with VALVEMATE 7040 control system (East Providence, R.I.). Other types of spray applicators, including air-assisted internal mixing atomizers and ultrasonic applicators can also be used for the application of the composition. A temperature controller 22 can be used for adjusting the temperature of the composition to a temperature other than room temperature. In the illustrated embodiment, temperature controller 22 circumscribes nozzle 18 portion of applicator 14 and is positioned in close proximity to orifice 20. In one implementation of the device, such placement of temperature controller 22 allows for the heating of nozzle 18 at a concentrated area so as to prevent prolonged exposure of the drug solution to the heat, which for heat sensitive drugs, such as actinomycin D, could prevent the degradation of the drug. The illustrated configuration allows the temperature of the composition to be adjusted contemporaneously with the spraying of the composition from nozzle 18. Heating of the solution will reduce surface tension and the viscosity of the solution, which are believed to be two key factors for achieving better coating uniformity and significantly minimizing the formation of "cob webs" between the stent struts and "pool webs" on the surface of the stent struts. Temperature controllers or thermal blocks are commercially available.

One commercial example is EUROTHERM (model 2416). A control modulator 23 can be provided for monitoring and controlling the temperature of controller 22 and, if desired, maintaining the temperature of the composition at a constant rate during the application of the composition. As one option, the temperature of the composition can be adjusted at barrel 12.

Implantable Devices

FIG. 1 additionally illustrates a stent 24 mounted on a mandrel 26. Mandrel 26 can be coupled to a motor assembly 28 for providing rotational motion and/or translational motion along railing 30 to stent 24. Stent is broadly intended to include self-expandable stents, balloon-expandable stents, and stent-grafts. One of ordinary skill in the art, however, understands that the apparatus and method of the invention can be used to coat other medical devices, such as grafts (e.g., aortic grafts), artificial heart valves, cerebrospinal fluid shunts, AXIUS coronary shunts (available from Guidant Corporation), pacemaker electrodes, and endocardial leads (e.g., FINELINE and ENDOTAK, available from Guidant Corporation). The underlying structure of the device can be virtually any design. Stents are typically defined by a tubular body having a network of bands or cylindrical elements interconnected by, for example, connecting elements. The particular structure of the stent is not of critical significance. The device can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used.

The Composition

The embodiments of the composition can be prepared by conventional methods wherein all components are combined, then blended. More particularly, in accordance with one embodiment, a predetermined amount of a polymer or combination of polymers can be added to a predetermined amount of a solvent or a combination of solvents. If necessary, heating, stirring and/or mixing can be employed to effect dissolution of the polymer(s) into the solvent(s)—for example in an 80° C. water bath for two hours. A therapeutic substance can be also added to the composition. The therapeutic substance should be in true solution or saturated in the blended composition. If the therapeutic substance is not completely soluble in the composition, operations including mixing, stirring, and/or agitation can be employed to effect homogeneity of the residues. The therapeutic substance may be added so that dispersion is in fine particles. The mixing of the therapeutic substance can be conducted at ambient pressure and at room temperature.

The polymer or combination of polymers chosen must be biocompatible and minimize irritation to the vessel wall when the device is implanted. The polymer may be either a biostable or a bioabsorbable polymer. Bioabsorbable polymers that could be used include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid. Also, biostable polymers with a relatively low chronic tissue response such as polyurethanes, silicones, and polyesters could be used. Other polymers include polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene fluoride and polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Ethylene vinyl alcohol is functionally a very suitable choice of polymer. The copolymer possesses good adhesive qualities to the surface of a stent, particularly stainless steel surfaces, and has illustrated the ability to expand with a stent without any significant detachment of the copolymer from the surface of the stent. The copolymer, moreover, allows for good control capabilities over the release rate of the therapeutic substance.

Representative examples of solvents include dimethylsulfoxide (DMSO), iso-propylalcohol (IPA), n-propylalcohol, tetrahydrofuran (THF), dimethylformamide (DMF), dimethyl acetamide (DMAC) or any other suitable solvent that is capable of placing the selected polymer into dissolution at the selected concentration and should not adversely react with the therapeutic substance.

The active agent could be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233, or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone.

The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Method of Applying the Composition

EFD spray device is an air-assisted external mixing atomizer. The composition is atomized into small droplets by air and uniformly applied to the stent surface. The atomization pressure can be maintained at a range of about 5 to 30 psi. The droplet size depends on such factors as viscosity of the solution, surface tension of the solvent, temperature of nozzle 18, and atomizing pressure.

During the application of the composition, stent 24 can be rotated about the stent's central longitudinal axis. Rotation of stent 24 can be from about 1 rpm to about 300 rpm, more narrowly about 50 rpm to about 150 rpm. By way of example, stent 24 can rotate at about 120 rpm. Stent 24 can also be a moved in a linear direction along the same axis. The stent can be moved at about 1 mm/sec. to about 12 mm/sec., for example about 6 mm/sec., for a minimum of at least two passes (i.e., back and forth passed the spray nozzle). The flow rate of the solution from the spray nozzle can be from about 0.01 mg/second to about 1.0 mg/second, for example about 0.1 mg/second.

For compositions having high viscosity and surface energy solvents (e.g., DMSO, DMAC, DMF, pyridine and dioxane), temperature controller 22 can be used to increase the temperature of applicator 14, more particularly nozzle 18 to a temperature above room temperature. Thus, the temperature of the composition leaving nozzle 18 would be greater than ambient temperature. For example, the temperature of the coating solution can be maintained between 35° C. to about 40° C. By increasing the temperature of the composition during the application of the composition to the stent, unexpected results have been achieved. Better coating uniformity and properties, such as lack of "cob webs" and "pool webs" have been observed by raising the temperature of the composition from ambient to between 35° C. to 40° C. By raising the temperature of the coating solution, the viscosity, surface energy, atomized droplet size of the solution can be reduced. Such effects have lead to improved wetting characteristics of the atomized solution on the metallic (e.g., stainless steel) surface of the stent. Another advantage gained by the apparatus of the present invention is the ability to increase the solid content in the solution, and thus deposit more coating per pass. Deposition of more solid content per pass leads to a reduction in the time of production of the stents.

In accordance with one embodiment, each repetition can be followed by removal of a significant amount of the solvent by application of a warm gas, such as air. The application of warm air between each repetition prevents coating defects and minimizes interaction between the active agent and the solvent. The temperature of the warm air can be about 30° C. to about 60° C., more narrowly about 40° C. to about 50° C. The flow rate of the warm air can be from about 20 cubic feet/minute (CFM) (0.57 cubic meters/minute(CMM)) to about 80 CFM (2.27 CMM), more narrowly about 30 CFM (0.85 CMM) to about 40 CFM (1.13 CMM). The warm air can be applied for about 3 seconds to about 60 seconds, more narrowly about 10 seconds to about 20 seconds. Applications can be performed at a temperature of about 50° C., the flow rate of about 40 CFM, and for about 10 seconds. Any suitable number of sets of application of the composition followed by blowing of warm air can be performed to form a coating of a desired thickness or weight. Excessive application of the polymer can, however, cause coating defects.

In accordance with one embodiment, the stent can be at least partially pre-expanded prior to the application of the composition. For example, the stent can be radially expanded about 20% to about 60%, more narrowly about 27% to about 55%—the measurement being taken from the stent's inner diameter at an unexpanded position to the inner diameter at the expanded position. The expansion of the stent, for increasing the interspace between the stent struts during the application of the composition, can further prevent "cob web" or "pool web" formation between the stent struts.

EXAMPLES

The following Examples are provided by way of illustration and not limitation.

Example 1

A Eurotherm (model 2416) heating block was coupled to the nozzle of an EFD spray applicator (EFD 780S spray device with VALVEMATE 7040 control system). A 2 wt % composition of EVAL in DMAC solution was made. 0.67 wt % actinomycin D was added to the solution. The temperature of the nozzle was increased from room temperature to about 40° C. The temperature was allowed to stabilize prior to the spray process. Atomization pressure was set at 15 psi and the solution barrel pressure was set at about 2 to 5 psi. The composition was applied to the stent at a flow rate of 0.7 mg/sec of solution. The stent was rotated at about 150 rpm and moved back and forth at about 6 mm/sec for 30 cycles (1 cycle=once back and forth passed the nozzle). The stent was dried by heated air at 55° C. for about 10 seconds. About 10 to 15 micrograms of coating was applied per cycle for a total of 400 micrograms. A 2 wt % of EVAL in DMAC solution was made for the topcoat solution. A rate-limiting barrier was then deposited on the drug matrix. The flow rate was set at 0.7 mg/sec of spray solution. A 400 microgram top-coat was deposited on the stent. The stent did not illustrate any significant formation of "cob webs."

Example 2

A Eurotherm (model 2416) heating block was coupled to the nozzle of an EFD spray applicator (EFD 780S spray device with VALVEMATE 7040 control system). A 4 wt % stock solution of EVAL in DMAC was made, to be used for the primer layer and the top-coat layer. 1.34 wt % of actinomycin D was added to a portion of the composition for the drug solution. The composition was applied to the stent at a flow rate of 1.5 mg/sec of spray solution (20 to 25 micrograms semi-dry pick-up weight of the stent per spray cycle) for a total of 400 micrograms of drug coat and 400 micrograms of topcoat. During the application of the composition, the stent was rotated at about 150 rpm and moved back and forth at about 6 mm/sec for 20 cycles for each coating layer. The atomization air pressure was set at 15 psi. The heating temperature was set at 50° C. for drug coat and 60° C. for the topcoat. The stents were dried by application of heated air at 60° C. for 10 seconds. The stent did not illustrate any significant formation of "cob webs."

While particular embodiments of the present invention have been shown and described, it will be obvious to those skilled in the art that changes and modifications can be made without departing from the embodiments this invention in its broader aspects and, therefore, the appended claims are to encompass within their scope all such changes and modifications as fall within the true spirit and scope of the embodiments this invention.

What is claimed is:

1. A method of coating a stent, comprising:
positioning a stent at a distance away from a nozzle;
applying a coating composition from the nozzle to the stent, the coating composition including a substance capable of degrading with exposure to heat; and
adjusting the temperature of the nozzle to heat the coating composition.

2. The method of claim 1, wherein the coating composition further includes a polymer dissolved in a solvent, and the substance capable of degrading with exposure to heat is a therapeutic substance.

3. The method of claim 1, additionally including rotating the stent about a longitudinal axis of the stent during the application of the coating composition.

4. The method of claim 1, wherein the coating composition is applied as atomized droplets.

5. The method of claim 1, wherein the temperature of the nozzle is adjusted prior to the application of the coating composition from the nozzle.

6. The method of claim 1, wherein the temperature of the nozzle is adjusted contemporaneously with the application of the coating composition from the nozzle.

7. The method of claim 1, wherein a thermal block is in thermal communication with the nozzle, the thermal block configured to adjust the temperature of the nozzle.

8. The method of claim 7, further comprising monitoring the temperature of the thermal block and making adjustments to the temperature of the thermal block based on the monitoring.

9. The method of claim 7, wherein the thermal block is positioned in close proximity to an orifice of the nozzle and circumscribes the nozzle.

10. The method of claim 1, wherein the temperature of the nozzle is adjusted to a temperature of about 35 degrees C. to about 40 degrees C.

11. The method of claim 1, wherein the temperature of the nozzle is adjusted to a temperature above 40 degrees C.

12. The method of claim 1, wherein the temperature of the nozzle is adjusted to a temperature above room temperature.

13. The method of claim 1, wherein the substance capable of degrading with exposure to heat is actinomycin D.

14. A method of coating a stent, comprising:
positioning a stent on a support apparatus;
spraying a coating composition from a nozzle to the stent positioned on the support apparatus, the coating composition including a heat sensitive substance; and
adjusting the temperature of the nozzle to heat the coating composition.

15. The method of claim 14, wherein the coating composition further includes a polymer dissolved in a solvent, and the heat sensitive substance is a therapeutic substance.

16. The method of claim 14, wherein the temperature of the nozzle is adjusted to a temperature of about 35° C. to 40° C.

17. The method of claim 14, wherein the temperature of the nozzle is adjusted to a temperature above room temperature.

18. The method of claim 14, additionally including rotating the stent about a longitudinal axis of the stent during spraying of the coating composition from the nozzle to the stent.

19. The method of claim 14, wherein the coating composition is sprayed as atomized droplets.

20. The method of claim 14, wherein the temperature of the nozzle is adjusted prior to the spraying of the coating composition from the nozzle.

21. The method of claim 14, wherein the temperature of the nozzle is adjusted contemporaneously with the spraying of the coating composition from the nozzle.

22. The method of claim 14, wherein adjusting the temperature of the nozzle includes activating a temperature controller coupled to the nozzle to heat the coating composition as the coating composition passes through the nozzle.

23. The method of claim 22, wherein the temperature controller is configured to heat the coating composition only at a concentrated area of the nozzle to prevent prolonged exposure of the coating composition to the heat.

24. The method of claim 22, further comprising monitoring the temperature of the temperature controller, and optionally, adjusting the temperature of the temperature controller based on the monitoring step.

25. The method of claim 22, wherein the temperature controller is activated to maintain the temperature of the coating composition at a constant temperature during the spraying process.

26. The method of claim 22, wherein the temperature controller is configured to change the temperature of the coating composition before the coating composition passes through an orifice of the nozzle and not after the composition passes through the orifice of the nozzle and in transit onto the stent.

27. The method of claim 14, wherein the temperature of the nozzle is adjusted by a thermal block in intimate, direct contact with the nozzle and circumscribing the nozzle.

28. The method of claim 27, further comprising monitoring the temperature of the thermal block and making adjustments based on the monitoring step.

29. The method of claim 27, wherein the thermal block is positioned in close proximity to an orifice of the nozzle.

30. The method of claim 14, wherein the temperature of the nozzle is adjusted to a temperature above 40 degrees C.

31. The method of claim 14, wherein the heat sensitive substance is actinomycin D.

* * * * *